United States Statutory Invention Registration [19]

[11] Reg. Number: H351

Kim et al. [43] Published: Oct. 6, 1987

[54] 4,4,10,10-TETRANITRO-6,8-DIOXATRIDECANE-1,13-DIOL POLYFORMAL AND METHOD OF PREPARATION

[75] Inventors: Kyung E. Kim, Potomac; Horst G. Adolph, Silver Spring, both of Md.

[73] Assignee: The United States of America as represented by the Secretary of the Navy, Washington, D.C.

[21] Appl. No.: 43,269

[22] Filed: Apr. 27, 1987

[51] Int. Cl.[4] ..... C08G 65/34; C07C 79/343; C07C 43/303; C06B 45/10

[52] U.S. Cl. ..... 528/266; 568/590; 568/944; 149/19.4; 149/19.6; 149/88

*Primary Examiner*—John F. Terapane
*Assistant Examiner*—J. E. Thomas
*Attorney, Agent, or Firm*—K. E. Walden; Roger D. Johnson

[57] ABSTRACT

4,4,10,10-tetranitro-6,8-dioxatridecane-1,13-diol polyformal, $HO(CH_2)_3C(NO_2)_2CH_2OCH_2OCH_2C(NO_2)_2(CH_2)_3O[CH_2O(CH_2)_3C(NO_2)_2CH_2OCH_2OCH_2C(NO_2)_2(CH_2)_3O]_nH$, which has high energy, high thermal stability, and which is useful as a prepolymer for plastic-bonded explosive compositions.

3 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

4,4,10,10-TETRANITRO-6,8-DIOXATRIDECANE-1,13-DIOL POLYFORMAL AND METHOD OF PREPARATION

BACKGROUND OF THE INVENTION

This invention relates to polyformals and more particularly to energetic polynitro polyformals.

Although a number of cross-linkable energetic polymers are known, most are not stable at 150° C. either because the energetic moiety (nitrato, azido) is not stable, or because the functional (end) groups are not stable. Polynitroalkyl acrylates can be cross-linked with di-acrylates, but the resulting three-dimensional polymers are hard and brittle and are not suitable for use as binders.

It would therefore be desirable to provide an energetic, flexible binder which is suitable for explosive compositions and which has a high degree of thermal stability.

SUMMARY OF THE INVENTION

Accordingly, an object of this invention is to provide a new energetic polymer which is suitable as a binder for explosive composites.

Another object of this invention is to provide a new energetic polynitro polyformal polymer which has a hydroxy functionality suitable for cross-linking.

A further object of this invention is to provide a new energetic polynitro polymer having improved thermal stability.

Yet another object of this invention is to provide a new polynitro homopolymer which has a glass transition point below room temperature.

These and other objects of this invention are accomplished by providing 4,4,10,10-tetranitro-6,8-dioxatridecane-1,13-diol polyformal, $HO(CH_2)_3C(NO_2)_2CH_2OCH_2OCH_2C(NO_2)_2(CH_2)_3O[CH_2O(CH_2)_3C(NO_2)_2CH_2OCH_2OCH_2C(NO_2)_2(CH_2)_3O]_nH$, which is prepared by the polycondensation of 4,4,10,10-Tetranitro-6,8-dioxatridecane-1,13-diol, $HO(CH_2)_3C(NO_2)_2CH_2OCH_2OCH_2C(NO_2)_2(CH_2)_3OH$, with formaldehyde. The polyformal is an energetic, thermally stable polymer which is useful in plastic bonded-explosive composites.

DETAILED DESCRIPTION OF THE PREFERRED EMBODIMENT 4,4,10,10-Tetranitro-6,8-dioxatridecane-1,13-diol polyformal, $HO(CH_2)_3C(NO_2)_2CH_2OCH_2OCH_2C(NO_2)_2(CH_2)_3O[CH_2O(CH_2)_3C(NO_2)_2CH_2OCH_2OCH_2C(NO_2)_2(CH_2)_3O]_nH$, is the first nitro homopolymer with a glass trans point below room temperature. The polymer is soluble in energetic nitroplasticizers such as (1) bis(2-fluoro-2,2-dinitroethyl)formal (FEFO) or (2) a mixture of bis(2,2-dinitropropyl)formal and bis(2,2-dinitropropyl)acetal (BDNPF/A), and these solutions can be crosslinked with commercially available polyisocyanates. As example 4 illustrates, a gumstock made with the polymer, FEFO plasticizer (1:3 ratio), and Desmodur N-100 polyisocyanate gave the same result in the vacuum thermal stability test at 150° C. as FEFO itself (0.1 mL/g/h; 7.5 mL/g/24 h). Thus, 4,4,10,10-tetranitro-6,8-dioxatridecane-1,13-diol polyformal is at least as thermally stable as FEFO. In summary, the properties of 4,4,10,10-tetranitro-6,8-dioxatridecane-1,13-diol polyformal show that it is a desirable energetic polymer or prepolymer, having a relatively low glass transition temperature, good thermal stability, and the required hydroxy functionallity for cross-linking.

In particular, 4,4,10,10-tetranitro-6,8-dioxatridecane-1,13-diol polyformal may be cured with polyisocyanates to produce rubbery polymers. Organic polyisocyanates which may be used in this invention include polymethylenepolyphenylisocyanate (PAPI), isophorone di- and triisocyanate mixtures, and N,N'N''-trisisocyanatohexybiuret. The polyisocyanate is used in an amount sufficient to supply from about 0.8:1 to about 1.5:1 but preferably from 1:1 to 1.2:1 isocyanate functional groups for each hydroxy functional group.

Plastic bonded explosives may be prepared from the uncured prepolymer/plasticizer mixture and conventional explosive ingredients using conventional process steps. First, the conventional explosive ingredients (solid explosive particles, fuels, additives, etc.) are mixed or loaded into the uncured prepolymer/plasticizer mixture in the formulated amounts. Next a calculated amount of polyisocyanate is added, along with any catalyst used, to the mixture. In each of these steps the mixture is thoroughly agitated (e.g., stirred), preferably under vacuum, to produce a uniform mixture. Finally, the mixture is cured, generally by heating, to produce the plastic-bonded explosive.

4,4,10,10-tetranitro-6,8-dioxatridecane-1,13-diol polyformal is prepared by the polycondensation of 4,4,10,10-tetranitro-6,8-dioxatridecane-1,3-diol with formaldehyde (e.g., trioxane) in the presence of a suitable catalyst such as $SnCl_4$, $BF_3$ etherate, $TiCl_4$, or $ZrCl_4$, with $SnCl_4$ being preferred:

$$HO(CH_2)_3C(NO_2)_2CH_2OCH_2OCH_2C(NO_2)_2(CH_2)_3OH + CH_2O \xrightarrow{SnCl_4}$$

$$HO(CH_2)_3C(NO_2)_2CH_2OCH_2OCH_2C(NO_2)_2(CH_2)_3O[CH_2O(CH_2)_3C(NO_2)_2CH_2OCH_2OCH_2C(NO_2)_2(CH_2)_3O]_nH$$

wherein $n>1$. The number average molecular weight of the polymer product can be adjusted by changing the diol:trioxane ratio, the amount of catalyst, and the amount of solvent. A number average molecular weight of from about 2,000 to about 4,000 is preferred for use as a prepolymer for plastic-bonded explosive binders.

The preferred reaction conditions are illustrated by Example 3. Care is taken to prevent overheating during the addition of the catalyst to the reactants. The reaction may then be run at room temperature (20° C.) with agitation (e.g., stirring).

The 4,4,10,10-tetranitro-6,8-dioxatridecane-1,13-diol starting material is prepared by the reduction of 4,4,10,10-tetranitro-6,8-dioxatridecane-1,13-dioate (CARFO):

$$CH_3OOCCH_2CH_2C(NO_2)_2CH_2OCH_2OCH_2C(NO_2)_2CH_2CH_2COOCH_3 \xrightarrow{BH_3.THF}$$

-continued $HOCH_2CH_2CH_2C(NO_2)_2CH_2OCH_2OCH_2C(NO_2)_2CH_2CH_2CH_2OH$

Conditions for the reduction are illustrated by Example 2. A prior art method of preparing CARFO is given in Example 1.

The general nature of the invention having been set forth, the following examples are presented as specific illustrations thereof. It will be understood that the invention is not limited to these specific examples but is susceptible to various modifications that will be recognized by one of ordinary skill in the art.

Example 1 illustrates a prior art method of producing the dimethyl 4,4,10,10-tetranitro-6,8-dioxatridecane-1,13-dioate starting material and is taken from Naval Ordnance Laboratory Technical Report number NOLTR 63-138 (K. G. Shipp, June 5, 1963).

EXAMPLE 1

Dimethyl 4,4,10,10-tetranitro-6,8-dioxatridecane-1,13-dioate; (CARFO)

(Prior Art)

A solution of 4.0 g, 0.1 mol, of sodium hydroxide in 15 mL of water and 15 mL of methanol was prepared in a 250 mL, 3-neck, creased round bottom flask fitted with a mechanical stirrer, thermometer and a dropping funnel. This solution was cooled to 0° C. by means of an ice and salt bath, and 12 mL of "30%" hydrogen peroxide was added slowly, keeping the temperature under 5° C. during the addition. A slurry of sodium hydroperoxide formed. To this slurry a solution of 7.4 g, 0.08 mol, of bis(2,2,2-trinitroethyl) formal, TEFO, in 30 mL of methanol was added during 20 minutes, keeping the temperature under 0° C. by the rate of addition. The resulting mixture was stirred for 45 minutes, the cooling bath was removed and a very little manganese dioxide was added to decompose excess hydrogen peroxide. Gas evolution ceased after ½ hour; water (about 25 mL) was added to dissolve all salts present and the mixture was filtered.

The clear yellow filtrate was placed in a 250 mL Erlenmeyer flask and 8.6 g, 0.1 mol, of methyl acrylate, 2.5 g, 0.04 mol, of glacial acetic acid, and 3 mL, 0.03 mol, of concentrated HCl were added. The solution rapidly became cherry red in color and a light yellow oil began to form almost immediately. Crystallization of the oil began after about two hours and the color of the supernatant solution changed to orange yellow. The mixture was stirred, magnetic stirring, over night when the solution was light orange yellow and the crystalline product almost colorless. The product was filtered off, washed well with water and dried. It weighed 8.0 g or 87.7% of the theoretical yield. Recrystallized twice from methanol and water (Darco & Celite), 6.5 g, 71.3% yield, of colorless needles, mp 70° C., was obtained from the crude product.

EXAMPLE 2

4,4,10,10-Tetranitro-6,8-dioxatridecane-1,13-diol

Dimethyl 4,4,10,10-tetranitro-6,8-dioxatridecane-1,13-dioate (28.8 g) was dissolved in 139 mL of $BH_3$.THF with ice-cooling and under a nitrogen atmosphere. The solution was stirred at room temperature for 3 days, after which time 27 mL of water was added slowly and the mixture was heated at 60° C. for 5 minutes. After cooling, the mixture was poured into 200 mL of water, and the product was extracted with ether. The ether solution was washed with aqueous sodium bicarbonate solution, then with water, and dried ($MgSO_4$) After removal of the solvent, the crude product was recrystallized from dichloromethane. Yield: 19.9 g (79%); M.P. 72.5°-3.5° C. $^1H$ NMR spectrum ($CDCl_3$/TMS): δ 4.76 (s, 2H); 4.41 (s, 4H); 2.69 (m, 4H); 1.59 (m. 4H).

EXAMPLE 3

4,4,10,10-Tetranitro-6,8-dioxatridecane-1,13-diol Polyformal

The diol (1.8 g) prepared in example 2 and 0.14 g of trioxane were dissolved, under a nitrogen atmosphere, in 1.5 mL of dry sulfolane. Dry dichloromethane (1 mL) was added, the solution was cooled in an ice-bath, and 0.25 mL of tin (IV) chloride was added. The mixture was stirred overnight at room temperature. The mixture was diluted with 4 mL of dichloromethane and then quenched with 4 mL of ice-cold water. The mixture was stirred for 2 hours, the dichloromethane layer was separated, washed with brine, dried ($MgSO_4$), and freed of solvent. To remove residual sulfolane, the crude polymer was triturated with water at 50° C. until no sulfolane peaks were discernable in the $^1H$ NMR spectrum. The yield of polymer was 1.38 g; $M_w=5290$, $M_n=2475$.

EXAMPLE 4

1.0 g of 4,4,10,10-tetranitro-6,8-dioxatridecane-1,13-diol polyformal of a number average molecular weight of 2475 and 3.0 g of bis(2-fluoro-2,2-dinitroethyl)formal (FEFO) were mixed until homogeneous. Then 0.14 g of Desmodur N-100 polyisocyanate was added and mixed with the FEFO-polymer solution. Then 0.00015 mL of dibutyl tin dilaurate catalyst was added and again mixed well with the FEFO-polymer-polyisocyanate solution. The 24 mixture was then heated to 50° C. under vacuum (≦1 mm) to remove dissolved and entrapped gases, and was then cured by storing at 50° C. for 48 hours. A rubbery gumstock was obtained. The thermal stability of this material was determined with the standard Vacuum Thermal Stability Test. The gas evolution was found to be 0.1 mL/g/h and 7.5 mL/g/24 h. Note: Desmodur N-100 is a hexamethylene diisocyanate based polyisocyanate composed of hexamethylene diisocyanate and a homopolymer of it. Desmodur N-100 is available from the Mobay Corporation, Coatings Division, Mobay Road, Pittsburgh, Pa. 15205—9741.

Obviously numerous modifications and variations of the present invention are possible in light of the above teachings. It is therefore to be understood that within the scope of the appended claims the invention may be practiced otherwise than as specifically described herein.

What is claimed is:

1. 4,4,10,10-tetranitro-6,8-dioxatridecane-1,13-diol.

2. 4,4,10,10-tetranitro-6,8-dioxatridecane-1,13-diol polyformal having the formula $HO(CH_2)_3C(NO_2)_2CH_2OCH_2OCH_2C(NO_2)_2(CH_2)_3O[CH_2O(CH_2)_3C(NO_2)_2CH_2OCH_2OCH_2C(NO_2)_2(CH_2)_3O]_nH$ wherein $n>1$.

3. The polyformal of claim 2 wherein the number average molecular weight $\overline{M}_n$ is from 2000 to 4000.

* * * * *